(12) United States Patent
Kaltenbach

(10) Patent No.: US 6,562,848 B1
(45) Date of Patent: May 13, 2003

(54) BIS-AMINO ACID SULFONAMIDES AS HIV PROTEASE INHIBITORS

(75) Inventor: Robert F. Kaltenbach, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/246,116

(22) Filed: Sep. 18, 2002

Related U.S. Application Data
(60) Provisional application No. 60/323,042, filed on Sep. 18, 2001.

(51) Int. Cl.$^7$ .................. A61K 31/44; C07D 213/46
(52) U.S. Cl. .................. 514/354; 514/354; 546/314; 549/449; 549/467; 564/123
(58) Field of Search .................. 514/354; 546/314; 549/467, 449; 564/123

(56) References Cited

U.S. PATENT DOCUMENTS

| 5,783,701 A | | 7/1998 | Tung et al. |
| 6,060,476 A | * | 5/2000 | Vazquez et al. ............ 514/256 |
| 6,143,788 A | | 11/2000 | Getman et al. |
| 6,147,051 A | | 11/2000 | Watanabe et al. |
| 6,150,556 A | | 11/2000 | Getman et al. |

FOREIGN PATENT DOCUMENTS

| JP | 05194254 | 8/1993 |
| WO | WO92200750 | 1/1992 |
| WO | WO9506030 | 3/1995 |
| WO | WO2000047551 | 8/2000 |
| WO | WO9628464 | 11/2000 |

* cited by examiner

*Primary Examiner*—Alan L. Rotman
*Assistant Examiner*—Janet L Coppins
(74) *Attorney, Agent, or Firm*—Mary K. Van Atten

(57) ABSTRACT

This invention relates generally to bis-amino acid sulfonamides containing substituted benzyl amines of formula I:

I

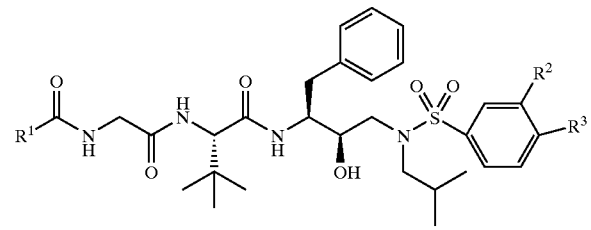

or stereoisomeric forms, stereoisomeric mixtures, or pharmaceutically acceptable salt forms thereof, which are useful as HIV protease inhibitors, pharmaceutical compositions and diagnostic kits comprising the same, methods of using the same for treating viral infection or as assay standards or reagents, and intermediates and processes for making the same.

20 Claims, No Drawings

BIS-AMINO ACID SULFONAMIDES AS HIV PROTEASE INHIBITORS

This application claims benefit of No. 60/323,042 Sep. 18, 2001.

FIELD OF THE INVENTION

This invention relates generally to bis-amino acid sulfonamides useful as HIV protease inhibitors, pharmaceutical compositions and diagnostic kits comprising the same, and methods of using the same for treating viral infection or as assay standards or reagents.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

The genomes of retroviruses encode a protease that is responsible for the proteolytic processing of one or more polyprotein precursors such as the pol and gag gene products. See Wellink, *Arch. Virol.* 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., *J. Virol.* 53 899 (1985); Katoh et al., *Virology* 145 280 (1985). Therefore, retroviral protease inhibition provides an attractive target for antiviral therapy. See Mitsuya, *Nature* 325 775 (1987).

As evidenced by the protease inhibitors presently marketed and in clinical trials, a wide variety of compounds have been studied as potential HIV protease inhibitors. One core, hydroxyethylamino-sulfonamides, has received significant attention. For example, PCT Applications WO94/05639, WO94/04492, WO95/06030, and WO96/28464 generically describe sulfonamides of the formula:

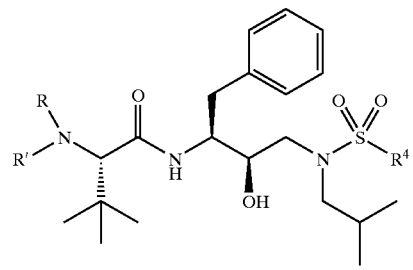

and methods of preparing them. Though some of the present compounds appear to fall within the generic descriptions of some of the above publications, they are not specifically disclosed, suggested, or claimed therein.

Even with the current success of protease inhibitors, it has been found that HIV patients can become resistant to a single protease inhibitor. Thus, it is desirable to develop additional protease inhibitors to further combat HIV infection.

SUMMARY OF THE INVENTION

Accordingly, one aspect of the present invention is to provide novel protease inhibitors.

The present invention provides a novel method for treating HIV infection which comprises administering to a host in need of such treatment a therapeutically effective amount of at least one of the compounds of the present invention or a pharmaceutically acceptable salt form thereof.

The present invention provides a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

The present invention provides pharmaceutical compositions with protease inhibiting activity comprising a pharmaceutically acceptable carrier and a therapeutically effective amount of at least-one of the compounds of the present invention or a pharmaceutically acceptable salt form thereof.

The present invention provides a method of inhibiting HIV present in a body fluid sample which comprises treating the body fluid sample with an effective amount of a compound of the present invention.

The present invention provides a kit or container containing at least one of the compounds of the present invention in an amount effective for use as a standard or reagent in a test or assay for determining the ability of a potential pharmaceutical to inhibit HIV protease, HIV growth, or both.

The present invention provides novel compounds for use in therapy.

The present invention provides the use of novel compounds for the manufacture of a medicament for the treatment of HIV infection.

These and other aspects, which will become apparent during the following detailed description, have been achieved by the inventors' discovery that compounds of formula (I):

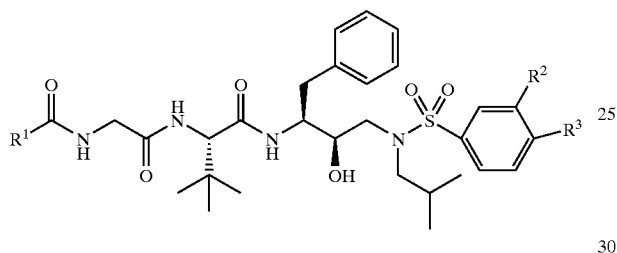

I wherein $R^1$, $R^2$, and $R^3$ are defined below, stereoisomeric forms, mixtures of stereoisomeric forms, or pharmaceutically acceptable salt forms thereof, are effective protease inhibitors.

DETAILED DESCRIPTION OF PREFERRED EMBODIMENTS

[1] Thus, in a first embodiment, the present invention provides a novel compound of Formula I:

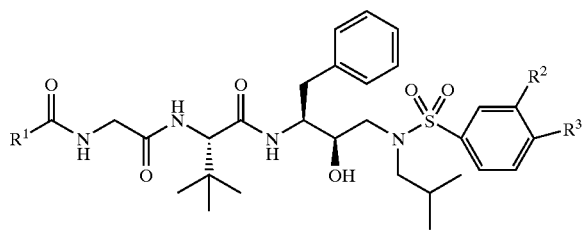

I or a pharmaceutically acceptable salt form thereof, wherein:

$R^1$ is selected from $R^4$ and —O—$R^4$;

$R^2$ and $R^3$ are selected from H and $NH_2$, or alternatively, $R^2$ and $R^3$ together form —$OCH_2O$— or —$CH_2CH_2O$—; and $R^4$ is selected from methyl, ethyl, propyl, isopropyl, butyl, i-butyl, t-butyl, phenyl, benzyl, cyclopentyl, 2-aminophenyl, 3-aminophenyl, 4-aminophenyl, 2-pyridyl, 3-pyridyl, and 4-pyridyl.

[2] In another embodiment, the present invention provides a novel compound of Formula I: wherein
$R^2$ is H; and
$R^3$ is $NH_2$.

[3] In another embodiment, the present invention provides a novel compound of Formula I: wherein
$R^4$ is selected from i-propyl, phenyl, cyclopentyl, 2-pyridyl and 3-pyridyl.

[4] In another embodiment, the present invention provides a novel compound of Formula I, wherein:
$R^1$ is $R^4$; and
$R^4$ is i-propyl.

[5] In another embodiment, the present invention provides a novel compound of Formula I, wherein:
$R^1$ is $R^4$; and
$R^4$ is phenyl, cyclopentyl, 2-pyridyl and 3-pyridyl.

[5] In another embodiment, the present invention provides a novel compound of Formula I, wherein:
$R^1$ is —O—$R^4$; and
$R^4$ is cyclopentyl.

[7] In another embodiment, the present invention provides a novel compound of Formula II:

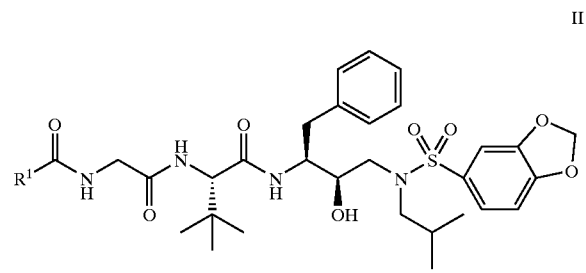

II or a pharmaceutically acceptable salt thereof.

[8] In another embodiment, the present invention provides a novel compound of Formula II, wherein:
$R^1$ is $R^4$; and
$R^4$ is methyl, ethyl, i-propyl, t-butyl, phenyl, and i-butyl.

[9] In another embodiment, the present invention provides a novel compound of Formula II, wherein:
$R^1$ is —O—$R^4$; and
$R^4$ is methyl, ethyl, i-propyl, cyclopentyl, phenyl, and benzyl.

[10] In another embodiment, the present invention provides a novel compound of Formula III, wherein:

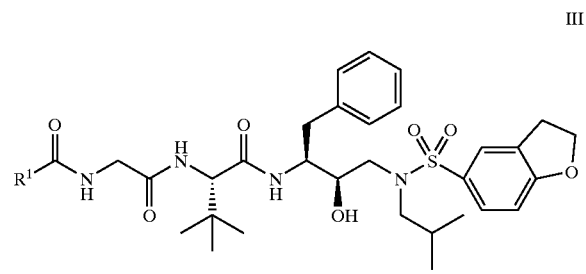

III or a pharmaceutically acceptable salt thereof.

[11] In another embodiment, the present invention provides a novel compound of Formula III: wherein
$R^1$ is $R^4$; and
$R^4$ is methyl, ethyl, and i-butyl.

[12] In another embodiment, the present invention provides a novel compound of Formula III, wherein:
$R^1$ is —O—$R^4$; and
$R^4$ is ethyl and i-propyl.

[13] In another embodiment, the present invention provides a novel compound of Formula II, wherein:

$R^1$ is $R^4$; and $R^4$ is selected from 2-aminophenyl, 3-aminophenyl, 4-aminophenyl, 2-pyridyl, 3-pyridyl, and 4-pyridyl.

[14] In another embodiment, the present invention provides novel compounds wherein the compound is selected from:

N-[(1-{3-[(4-Amino-benzenesulfonyl)-isobutyl-amino]-1-benzyl-2-hydroxy-propylcarbamoyl}-2,2-dimethyl-propylcarbamoyl)-methyl]-nicotinamide;

Pyridine-2-carboxylic acid [(1-{3-[(4-amino-benzenesulfonyl)-isobutyl-amino]-1-benzyl-2-hydroxy-propylcarbamoyl}-2,2-dimethyl-propylcarbamoyl)-methyl]-amide;

[(1-{3-[(4-Amino-benzenesulfonyl)-isobutyl-amino]-1-benzyl-2-hydroxy-propylcarbamoyl}-2,2-dimethyl-propylcarbamoyl)-methyl]-carbamic acid cyclopentyl ester;

[(1-{1-Benzyl-3-[(2,3-dihydro-benzofuran-5-sulfonyl)-isobutyl-amino]-2-hydroxy-propylcarbamoyl}-2,2-dimethyl-propylcarbamoyl)-methyl]-carbamic acid isopropyl ester;

[(1-{1-Benzyl-3-[(2,3-dihydro-benzofuran-5-sulfonyl)-isobutyl-amino]-2-hydroxy-propylcarbamoyl}-2,2-dimethyl-propylcarbamoyl)-methyl]-carbamic acid ethyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid benzyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid phenyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid phenyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid cyclopentyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid isopropyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid ethyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid methyl ester;

N-[(1-{3-[(4-Amino-benzenesulfonyl)-isobutyl-amino]-1-benzyl-2-hydroxy-propylcarbamoyl}-2,2-dimethyl-propylcarbamoyl)-methyl]-benzamide;

N-{3-[(4-Amino-benzenesulfonyl)-isobutyl-amino]-1-benzyl-2-hydroxy-propyl}-2-(2-isobutyrylamino-acetylamino)-3,3-dimethyl-butyramide;

N-{1-Benzyl-2-hydroxy-3-[isobutyl-(4-nitro-benzenesulfonyl)-amino]-propyl}-2-(2-isobutyrylamino-acetylamino)-3,3-dimethyl-butyramide;

N-{1-Benzyl-3-[(2,3-dihydro-benzofuran-5-sulfonyl)-isobutyl-amino]-2-hydroxy-propyl}-3,3-dimethyl-2-[2-(3-methyl-butyrylamino)-acetylamino]-butyramide;

N-{1-Benzyl-3-[(2,3-dihydro-benzofuran-5-sulfonyl)-isobutyl-amino]-2-hydroxy-propyl}-3,3-dimethyl-2-(2-propionylamino-acetylamino)-butyramide;

2-(2-Acetylamino-acetylamino)-N-{1-benzyl-3-[(2,3-dihydro-benzofuran-5-sulfonyl)-isobutyl-amino]-2-hydroxy-propyl}-3,3-dimethyl-butyramide;

N-[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-isonicotinamide;

N-[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-nicotinamide;

Pyridine-2-carboxylic acid [(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-amide;

4-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

3-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

2-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

2-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

N-{3-[(Benzo[1,3]dioxole-5-sulfonyl)-isobutyl-amino]-1-benzyl-2-hydroxy-propyl}-3,3-dimethyl-2-[2-(3-methyl-butyrylamino)-acetylamino]-butyramide;

N-[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

N-{3-[(Benzo[1,3]dioxole-5-sulfonyl)-isobutyl-amino]-1-benzyl-2-hydroxy-propyl}-2-[2-(2,2-dimethyl-propionylamino)-acetylamino]-3,3-dimethyl-butyramide;

N-{3-[(Benzo[1,3]dioxole-5-sulfonyl)-isobutyl-amino]-1-benzyl-2-hydroxy-propyl}-3,3-dimethyl-2-(2-propionylamino-acetylamino)-butyramide;

2-(2-Acetylamino-acetylamino)-N-{3-[(benzo[1,3]dioxole-5-sulfonyl)-isobutyl-amino]-1-benzyl-2-hydroxy-propyl}-3,3-dimethyl-butyramide; and N-{3-[(Benzo[1,3]dioxole-5-sulfonyl)-isobutyl-amino]-1-benzyl-2-hydroxy-propyl}-2-(2-isobutyrylamino-acetylamino)-3,3-dimethyl-butyramide.

In another embodiment, the present invention provides a novel pharmaceutical composition comprising a pharmaceutically acceptable carrier and a therapeutically effective amount of a compound of formula I, II or III, or pharmaceutically acceptable salt form thereof.

In another embodiment, the present invention provides a novel method for treating HIV infection which comprises administering to a host in need of such treatment a therapeutically effective amount of a compound of formula I, II or III, or pharmaceutically acceptable salt form thereof.

In another embodiment, the present invention provides a novel method of treating HIV infection which comprises administering, in combination, to a host in need thereof a therapeutically effective amount of:

(a) a compound of formula I, II or III; and, (b) at least one compound selected from the group consisting of HIV reverse transcriptase inhibitors and HIV protease inhibitors.

In another embodiment, the reverse transcriptase inhibitor is selected from the group AZT, ddC, ddI, d4T, 3TC, delavirdine, efavirenz, nevirapine, Ro 18,893, trovirdine, MKC-442, HBY 097, ACT, UC-781, UC-782, RD4-2025, and MEN 10979, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In another embodiment, the reverse transcriptase inhibitor is selected from the group AZT, efavirenz, and 3TC and the protease inhibitor is selected from the group saquinavir, ritonavir, nelfinavir, and indinavir.

In a still other embodiment, the reverse transcriptase inhibitor is AZT.

In another embodiment, the protease inhibitor is ritonavir.

In another embodiment, component (b) is a HIV reverse transcriptase inhibitor and a HIV protease inhibitor.

In another embodiment, component (b) is two different HIV reverse transcriptase inhibitors.

In another embodiment, the present invention provides a pharmaceutical composition useful for the treatment of HIV infection, which comprises a therapeutically effective amount of:

(a) a compound of formula I, II, or III; and, (b) at least one compound selected from the group consisting of HIV reverse transcriptase inhibitors and HIV protease inhibitors, in one or more sterile containers.

In another embodiment, the present invention provides a novel method of inhibiting HIV present in a body fluid sample which comprises treating the body fluid sample with an effective amount of a compound of formula I, II, or III.

In a ninth embodiment, the present invention to provides a novel kit or container comprising a compound of formula I, II, or III in an amount effective for use as a standard or reagent in a test or assay for determining the ability of a potential pharmaceutical to inhibit HIV protease, HIV growth, or both.

In another embodiment, the present invention provides novel compounds for use in therapy.

In another embodiment, the present invention provides he use of novel compounds for the manufacture of a medicament for the treatment of HIV infection.

Definitions

As used herein, the following terms and expressions have the indicated meanings. It will be appreciated that he compounds of the present invention contain symmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are not limited to, delavirdine (Pharmacia and Upjohn, U90152S), efavirenz (DuPont), nevirapine (Boehringer Ingelheim), Ro 18,893 (Roche), trovirdine (Lilly), MKC-442 (Triangle), HBY 097 (Hoechst), HBY 1293 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), tipranavir (Pharmacia and Upjohn, U-140690), DMP-450 (DuPont) and ABT-378.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to formula (I) or other formulas or compounds of the present invention in vivo when such prodrug is administered to a mammalian subject. Prodrugs of a compound of the present invention, for example formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups in the compounds of the present invention, and the like.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced. "Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

One diastereomer of a compound of Formula I may display superior activity compared with the other. When required, separation of the racemic material can be achieved by HPLC using a chiral column or by a resolution using a resolving agent such as camphonic chloride as in Thomas J. Tucker, et al, *J. Med. Chem.* 1994, 37, 2437–2444. A chiral compound of Formula I may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "°C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, and "TLC" for thin layer chromatography.

The preparation of compounds 1A, 2A, 3A, and 7A in the schemes described below are described in U.S. Pat. No. 6,391,919, issued May 21, 2002, which is hereby incorporated by reference.

Example 1

Scheme 1:

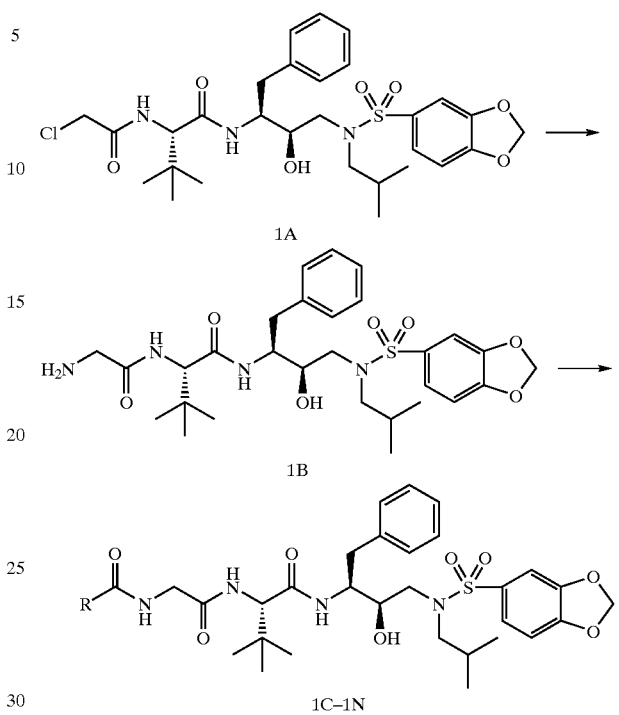

Example 1B

To a solution of N-[2R-hydroxy-3-[[(1,3-benzodioxol-5-yl)sulfonyl](2-methylpropyl)amino]-1S-(phenylmethyl)propyl]-2S-[(chloroacetyl)amino]-3,3-dimethylbutanamide 1A (15 g, 24.6 mmol) in THF (150 mL) and methanol (90 mL) was added ammonium hydroxide (225 mL, 30% aqueous). After stirring 4 days the solvent was removed under reduced pressure and the residue was chromatographed (silica gel, 10% methanol/CH$_2$Cl$_2$) to give the amine 1B as a white solid (13.47 g, 93%): $^1$H NMR (CDCl$_3$)δ7.75 (d, J=9.1 Hz, 1H), 7.34 (dd, J=8.1, 1.8 Hz, 1H), 7.24 (m, 6H), 6.88 (d, J=8.4 Hz, 1H), 6.63 (d, J=8.4 Hz, 1H), 6.09 (s, 2H), 4.27 (m, 1H), 4.13 (d, J=9.1 Hz, 1H), 3.86 (m, 1H), 3.30 (s, 2H), 3.20–2.83 (m, 6H), 1.86 (m, 1H), 0.88 (s, 9 H), 0.87 (d, J=6.0 Hz, 6H); IR (KBr)ν 3310, 2961, 1651, 1479 cm$^{-1}$; CIMS (NH$_3$) m/z: 591 (M+H$^+$, 100%).

1C

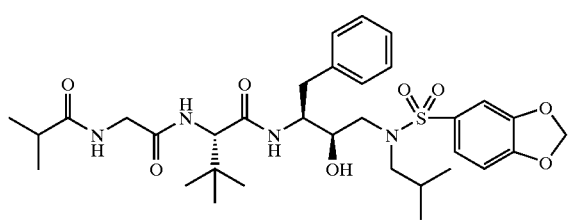

Example 1C

To a solution of amine 1B (2.0 g, 3.38 mmol) in THF (75 mL) was added triethylamine (2.73 g, 27.0 mmol) and isobutyryl chloride (448 mg, 4.21 mmol). After stirring 30 min the reaction mixture was diluted with EtOAc, washed with water, 5% citric acid, water, saturated NaHCO₃, brine, and was dried (MgSO₄). The solvent was removed under reduced pressure and the residue was recrystallized (ethyl acetate/hexane) to give the amide 1C as a white solid (1.39 g, 62%): mp 205–206° C.; $^1$H NMR (CDCl₃)δ7.35 (dd, J=8.1, 1.8 Hz, 1H), 7.21 (m, 6H), 6.87 (d, J=8.1 Hz, 1H), 6.74 (d, J=8.8 Hz, 1H), 6.58 (d, J=8.8 Hz, 1H), 6.46 (t, J=5.2 Hz, 1H), 6.09 (s, 2H), 4.26 (m, 1H), 4.08 (m, 2H), 3.85 (m, 3H), 3.18–2.80 (m, 6H), 2.48 (m, 1H), 1.85 (m, 1H), 1.19 (d, J=6.9 Hz, 3H), 1.18 (d, J=6.9 Hz, 3H), 0.88 (d, J=6.6 Hz, 6H), 0.85 (s, 9H); IR (KBr)ν 3492, 3286, 2964, 1633 cm⁻¹; CIMS (NH₃) m/z: 661 (M+H⁺, 100%). Anal. (C₃₃H₄₈N₄O₈S₁): Calc: C, 59.98; H, 7.32; N, 8.49. Found: C, 59.80; H, 7.30; N, 8.33.

1D

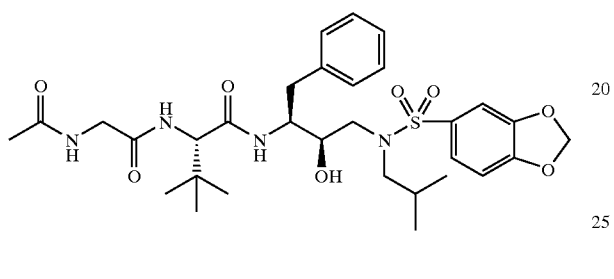

Example 1D

Prepared from the amine 1B and acetyl chloride following the procedure described for Example 1C: CIMS (NH₃) m/z: 633 (M+H⁺, 100%).

1E

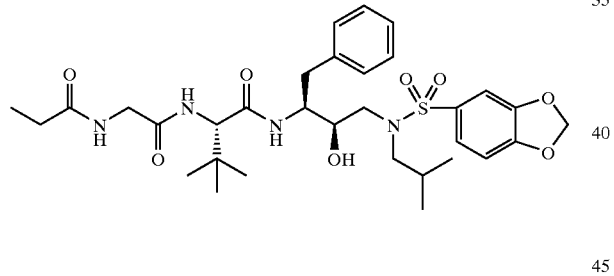

Example 1E

Prepared from the amine 1B and propionyl chloride following the procedure described for Example 1C: CIMS (NH₃) m/z: 647 (M+H⁺, 100%).

1F

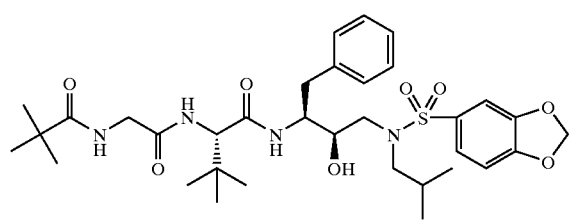

Example 1F

Prepared from the amine 1B and pivaloyl chloride following the procedure described for Example 1C: CIMS (NH₃) m/z: 675 (M+H⁺, 100%).

1G

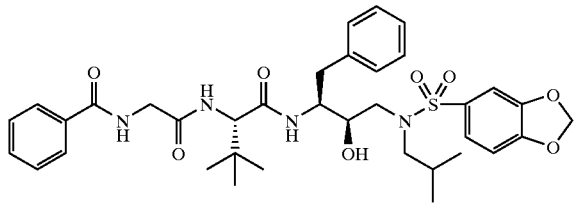

Example 1G

Prepared from the amine 1B and benzoyl chloride following the procedure described for Example 1C: CIMS NH₃) m/z: 695 (M+H⁺$^{b,\ 100}$%).

1H

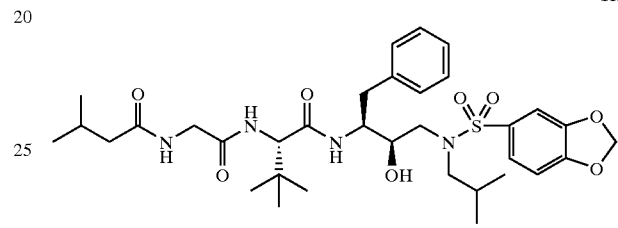

Example 1H

Prepared from the amine 1B and isovaleryl chloride following the procedure described for Example 1C: CIMS (NH₃) m/z: 675 (M+H⁺, 100%).

1I

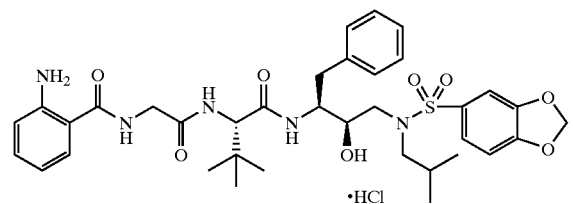

Example 1I

To a solution of amine 1B (1.0 g, 1.69 mmol) in THF (40 mL) was added triethylamine (1.27 g, 12.5 mmol) and 2-nitrobenzoyl chloride (371 mg, 2.0 mmol). After stirring 30 min the reaction mixture was diluted with EtOAc, washed with water, 5% citric acid, water, saturated NaHCO₃, brine, and was dried (MgSO₄). The solvent was removed under reduced pressure and the residue was recrystallized (ethyl acetate/hexane) to give the am ide as a white solid. The amide was taken up in methanol (50 mL) and CH₂Cl₂ (50 mL) and 20%Pd(OH)₂/C (250 mg) was added. The suspension was stirred overnight under an atmosphere of hydrogen. The mixture was filtered through Celite and the solvent was removed under reduced pressure. The residue was taken up in EtOAc (75 mL) and was treated with 4N HCl in dioxane (0.4 mL, 1.6 mmol). The resulting suspension was concentrated, diluted with ether and filtered to give the amide 1I as a white solid (698 mg, 55%): ESI m/z: 732 (M+Na⁺, 100%)

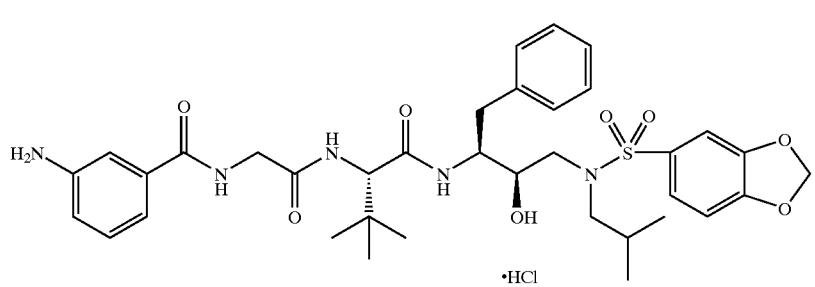

1J

Example 1J

Prepared from the amine 1B and 3-nitrobenzoyl chloride following the procedure described for Example 1I: ESI m/z: 732 (M+Na$^+$, 100%)

reduced pressure. The residue was taken up in ether/EtOAc and was treated with 4N HCl in dioxane (0.25 mL, 1.0 mmol). The resulting suspension was diluted with ether and filtered to give the amide 1L as a white solid (495 mg, 68%): CIMS (NH$_3$) m/z: 696 (M+H$^+$, 100%).

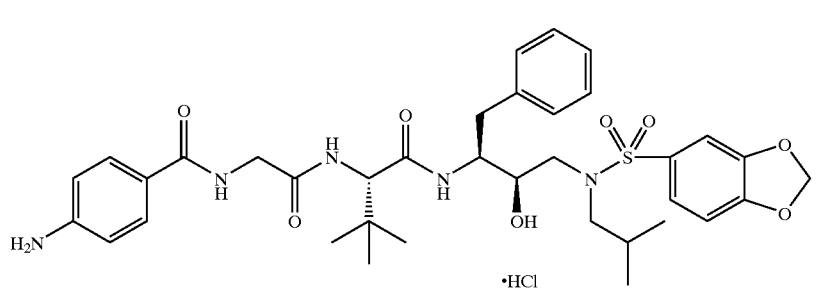

1K

Example 1K

Prepared from the amine 1B and 4-nitrobenzoyl chloride following the procedure described for Example 1I: ESI m/z: 732 (M+Na$^+$, 100%)

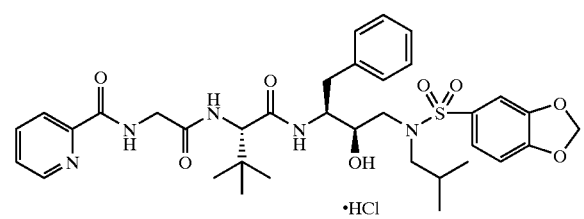

1L

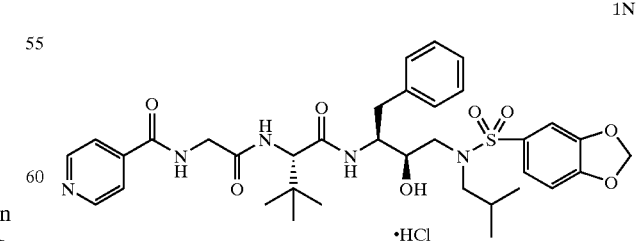

1M

Example 1M

Prepared from the amine 1B and nicotinic acid following the procedure described for Example 1L: CIMS (NH$_3$) m/z: 696 (M+H$^+$, 100%).

Example 1L

To a solution of picolinic acid (153 mg, 1.25 mmol) in THF (2 mL) was added 1,1'-carbonyldiimidazole (202 mg, 1.25 mmol). After stirring 1 h, the amine 1B (590 mg, 1.0 mmol) was added and the solution was stirred 3 h. The mixture was diluted with EtOAc, was washed with water, and was dried (MgSO$_4$). The solvent was removed under

1N

Example 1N

Prepared from the amine 1B and isonicotinic acid following the procedure described for Example 1L: CIMS (NH$_3$) m/z: 696 (M+H$^+$, 100%).

Scheme 2:

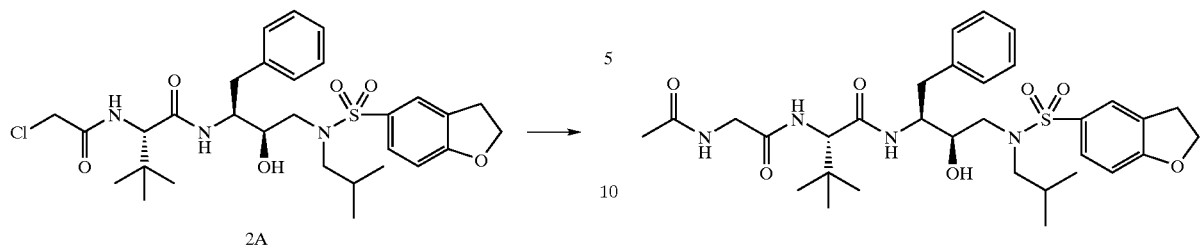

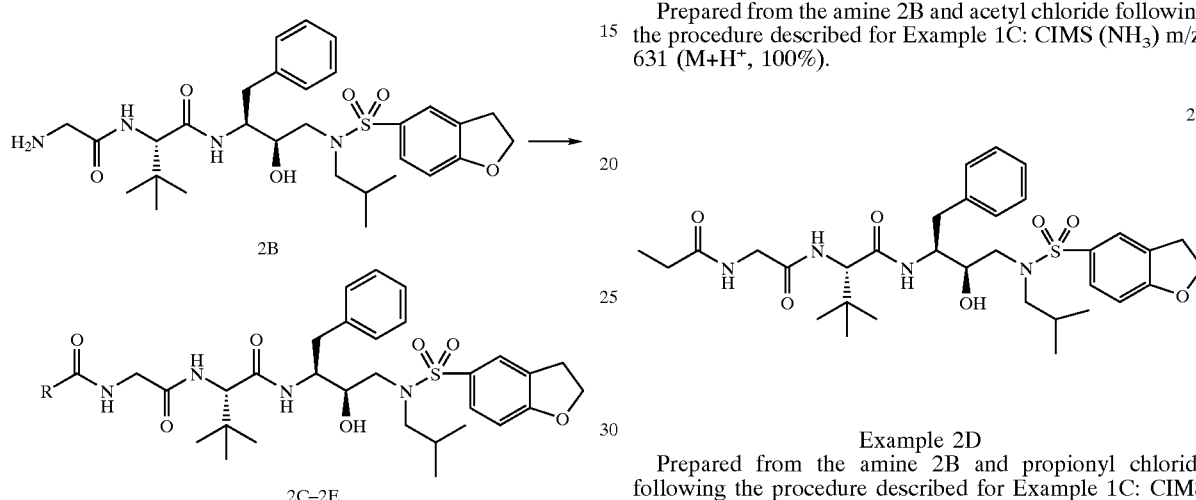

Example 2B

Prepared from N-[2R-hydroxy-3-[[(2,3-dihydrobenzofuran-5-yl)sulfonyl](2-methylpropyl)amino]-1S-(phenylmethyl)propyl]-2S-[(chloroacetyl)amino]-3,3-dimethylbutanamide 2A and ammonium hydroxide following the procedure described for Example 1B: CIMS (NH$_3$) m/z: 589 (M+H$^+$, 100%).

Example 2C

Prepared from the amine 2B and acetyl chloride following the procedure described for Example 1C: CIMS (NH$_3$) m/z: 631 (M+H$^+$, 100%).

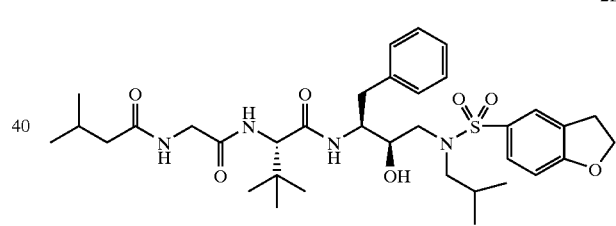

Example 2D

Prepared from the amine 2B and propionyl chloride following the procedure described for Example 1C: CIMS (NH$_3$) m/z: 645 (M+H$^+$, 100%).

Example 2E

Prepared from the amine 2B and isovaleryl chloride following the procedure described for Example 1C: CIMS (NH$_3$) m/z: 673 (M+H$^+$, 100%).

Scheme 3

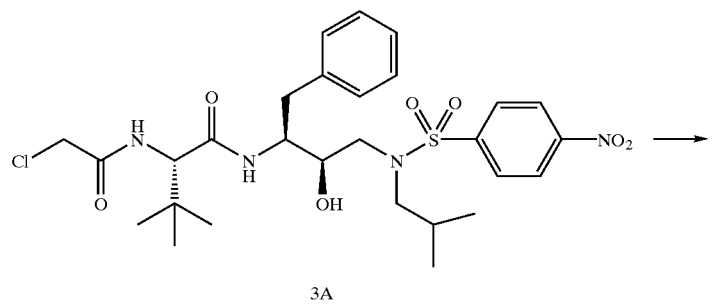

-continued

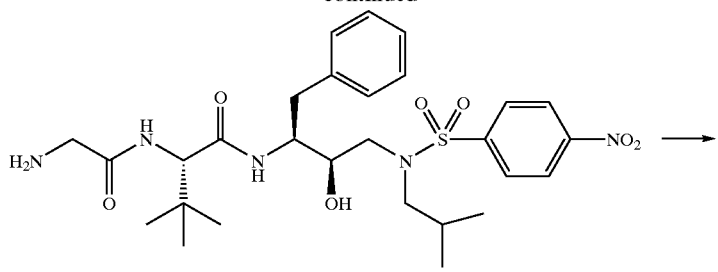

3B

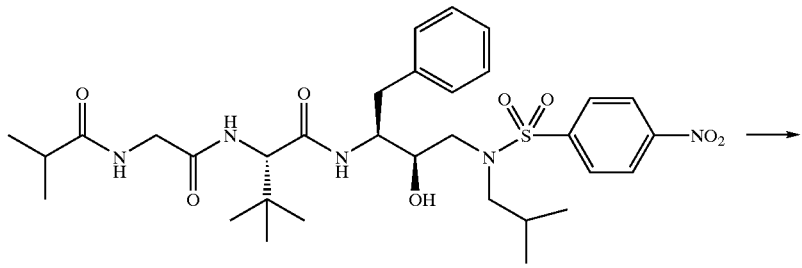

3C

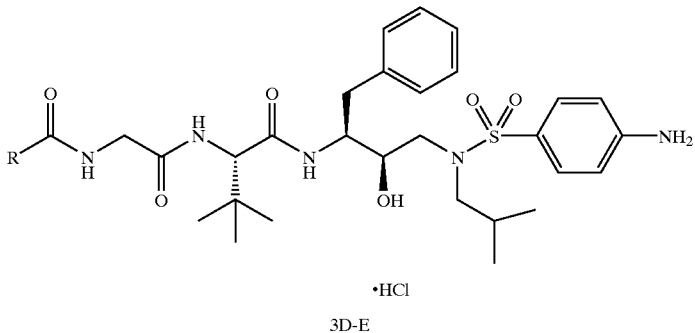

3D-E

Example 3B

To a solution of N-[2R-hydroxy-3-[[(4-nitrophenyl)sulfonyl](2-methylpropyl)amino]-1S-(phenylmethyl)propyl]-2S-[(chloroacetyl)amino]-3,3-dimethylbutanamide 3a (1.0 g, 1.63 mmol) in THF (10 mL) and methanol (6 mL) was added ammonium hydroxide (15 mL, 30% aqueous). After stirring 3 days the solvent was removed under reduced pressure and the residue was chromatographed (silica gel, 10% methanol/CH$_2$Cl$_2$) to give the amine 3B as a white solid (697 mg, 72%): APcI m/z: 592 (M+H$^+$, 100%).

3C

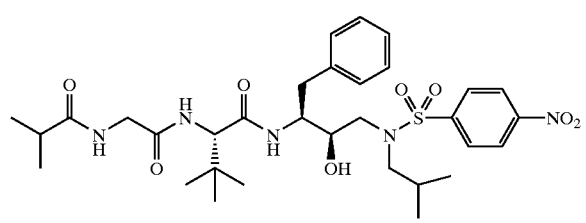

Example 3C

To a solution of amine 3B (117 mg, 0.198 mmol) in THF (5 mL) was added triethylamine (200 mg, 1.97 mmol) and isobutyryl chloride (127 mg, 1.17 mmol). After stirring 3 h the reaction mixture was diluted with EtOAc, washed with water, 5% citric acid, water, saturated NaHCO$_3$, brine, and was dried (MgSO$_4$). The solvent was removed under reduced pressure and the residue was chromatographed (silica gel, 10% methanol/CH$_2$Cl$_2$) to give the amide 3C as a white solid (96 mg, 73%): APcI m/z: 662 (M+H$^+$, 100%).

3D

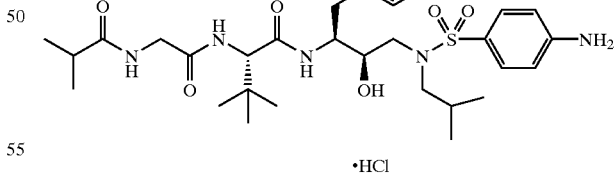

Example 3D

A suspension if the amide 3C (96 mg, 0.145 mmol) and 20%Pd(OH)$_2$/C (30 mg) in methanol (20 mL) was stirred 3 h under an atmosphere of hydrogen. The mixture was filtered through Celite, the solvent was removed under reduced pressure and the residue was chromatographed (silica gel, 5% methanol/CH$_2$Cl$_2$). The freebase was taken up in ether/EtOAc and was treated with 4N HCl in dioxane (0.05 mL, 0.2 mmol). The resulting suspension was diluted with ether and filtered to give the amide 3D as a white solid (41 mg, 31%): APcI m/z: 632 (M+H$^+$, 100%).

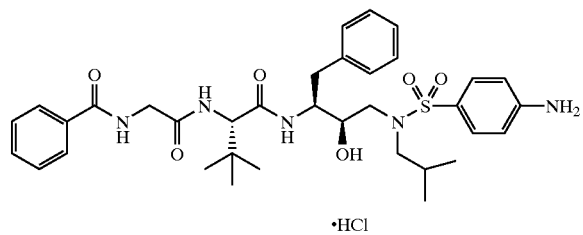

3E

·HCl

Example 3E

Prepared from the amine 3B and benzoyl chloride following the procedures described for Example 3C and 3D: ESI m/z: 688 (M+Na$^+$, 100%);

Scheme 4

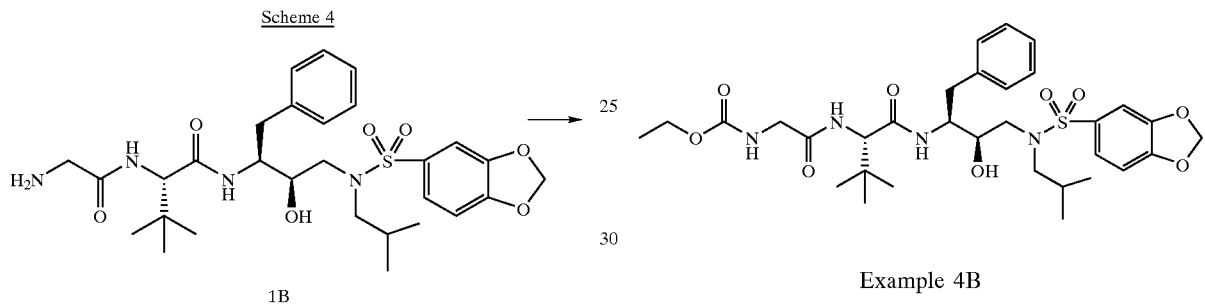

1B

4A-F

4A

Example 4A

To a solution of amine 1B (50 mg, 0.085 mmol) in CH$_2$Cl$_2$ (2 mL) was added triethylamine (85 mg, 0.84 mmol) and methyl chloroformate (38 mg, 0.40 mmol). After stirring 1 h the reaction mixture was diluted with EtOAc, washed with water, 1N HCl, water, saturated NaHCO$_3$ and was dried (MgSO$_4$). The solvent was removed under reduced pressure and the residue was chromatographed (silica gel, 5% methanol/CH$_2$Cl$_2$) to give the carbamate 4A as a white solid (30 mg, 55%): mp 85–186° C.; $^1$H NMR (CDCl$_3$)67 7.35 (dd, J=8.1, 1.8 Hz, 1H), 7.22 (m, 6H), 6.88 (d, J=8.1 Hz, 1H), 6.35 (m, 2H), 6.09 (s, 2H), 5.35 (br s, 1H), 4.22 (m, 1H), 4.08 (m, 1H), 3.98 (br s, 1H), 3.83 (m, 3H), 3.74 (s, 3H), 3.08–2.82 (m, 6H), 1.85 (m, 1H), 0.90 (d, J=6.3 Hz, 3H), 0.89 (d, J=6.3 Hz, 3H), 0.84 (s, 9H); IR (KBr)v 3290, 1695, 1634, 1526 cm$^{-1}$; CIMS (NH$_3$) m/z: 649 (M+H$^+$, 100%). Anal. (C$_{31}$H$_{44}$N$_4$O$_9$S$_1$) : Calc: C, 57.39; H, 6.85; N, 8.65. Found: C, 57.28; H, 6.72; N, 8.44.

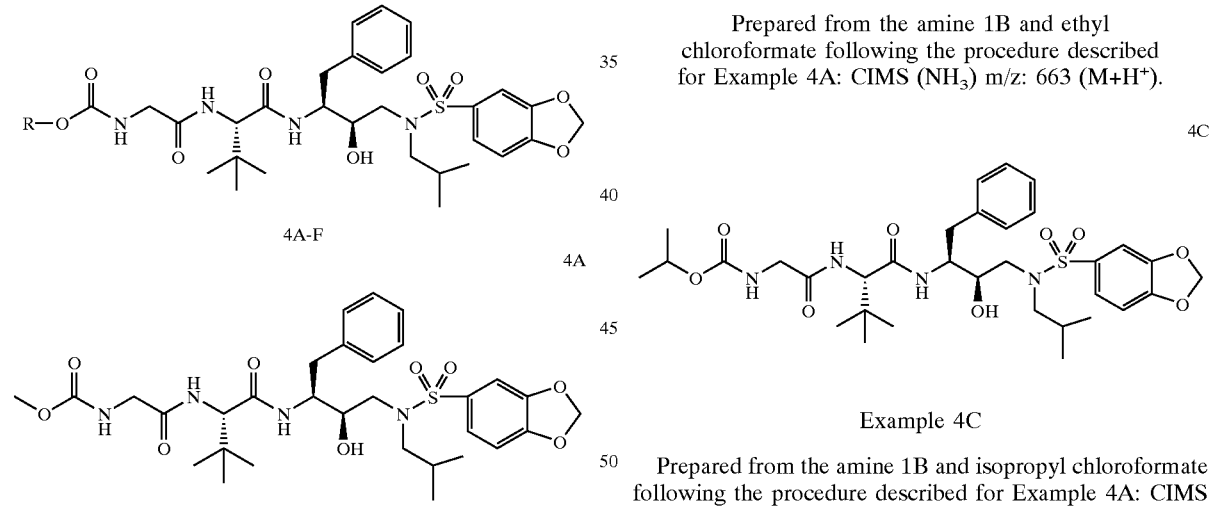

4B

Example 4B

Prepared from the amine 1B and ethyl chloroformate following the procedure described for Example 4A: CIMS (NH$_3$) m/z: 663 (M+H$^+$).

4C

Example 4C

Prepared from the amine 1B and isopropyl chloroformate following the procedure described for Example 4A: CIMS (NH$_3$) m/z: 677 (M+H$^+$).

4D

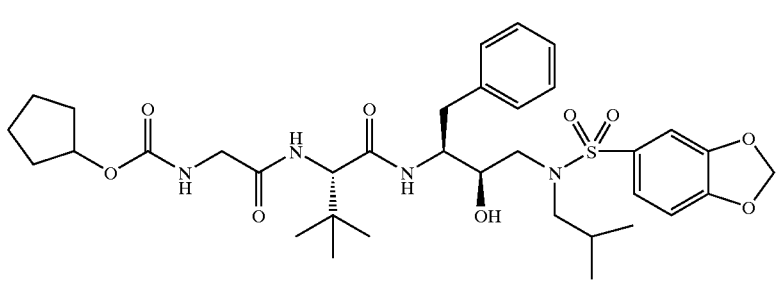

Example 4D

Prepared from the amine 1B and cyclopentyl chloroformate following the procedure described for Example 4A: CIMS (NH$_3$) m/z: 703 (M+H$^+$).

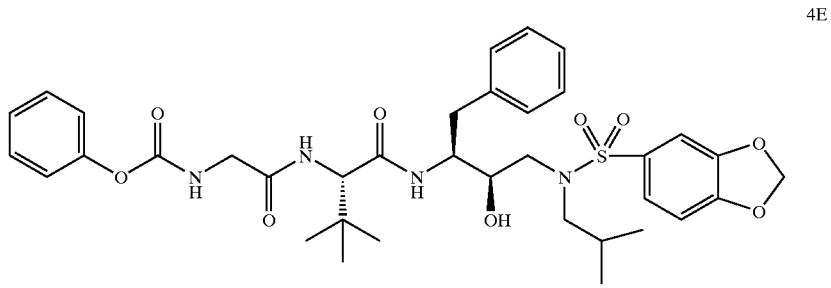

Example 4E

Example 4E

Prepared from the amine 1B and phenyl chloroformate following the procedure described for Example 4A: ESI m/z: 711 (M+H$^+$)

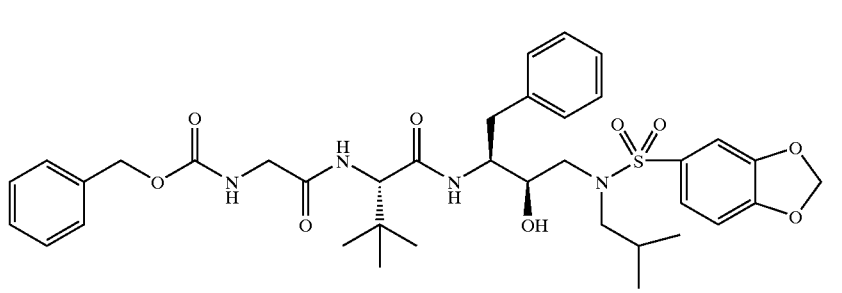

Example 4F

Example 4F

Prepared from the amine 1B and benzyl chloroformate following the procedure described for Example 4A: APcI m/z: 725 (M+H$^+$).

Scheme 5

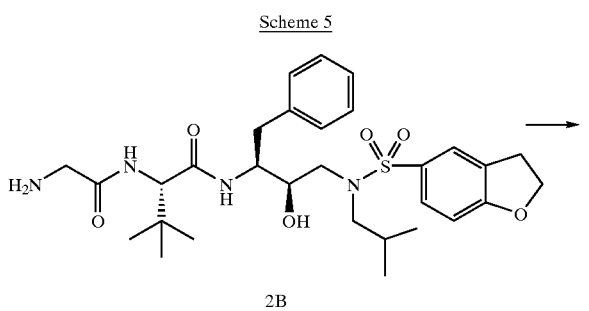

2B

-continued

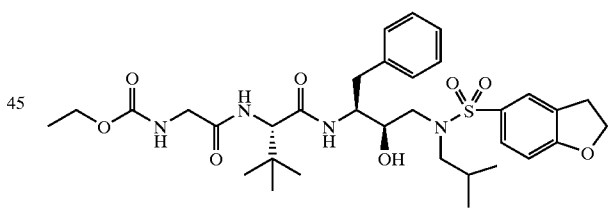

Example 5A

Example 5A

Prepared from the amine 2B and ethyl chloroformate following the procedure described for Example 4A: CIMS (NH$_3$) m/z: 661 (M+H$^+$).

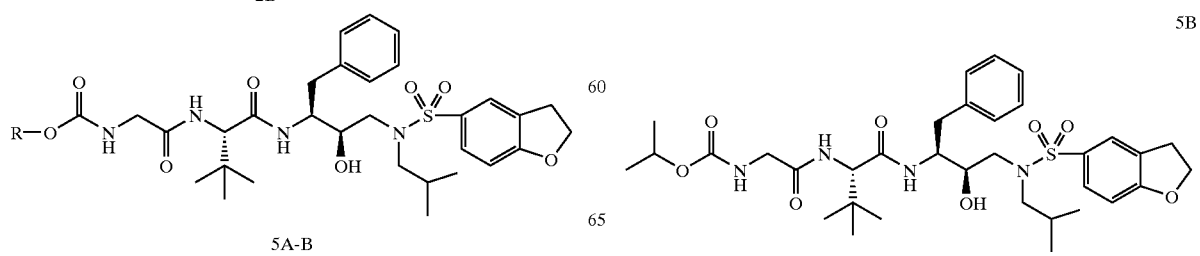

5A-B

Example 5B
Prepared from the amine 2B and isopropyl chloroformate following the procedure described for Example 4A: CIMS (NH$_3$) m/z: 675 (M+H$^+$).
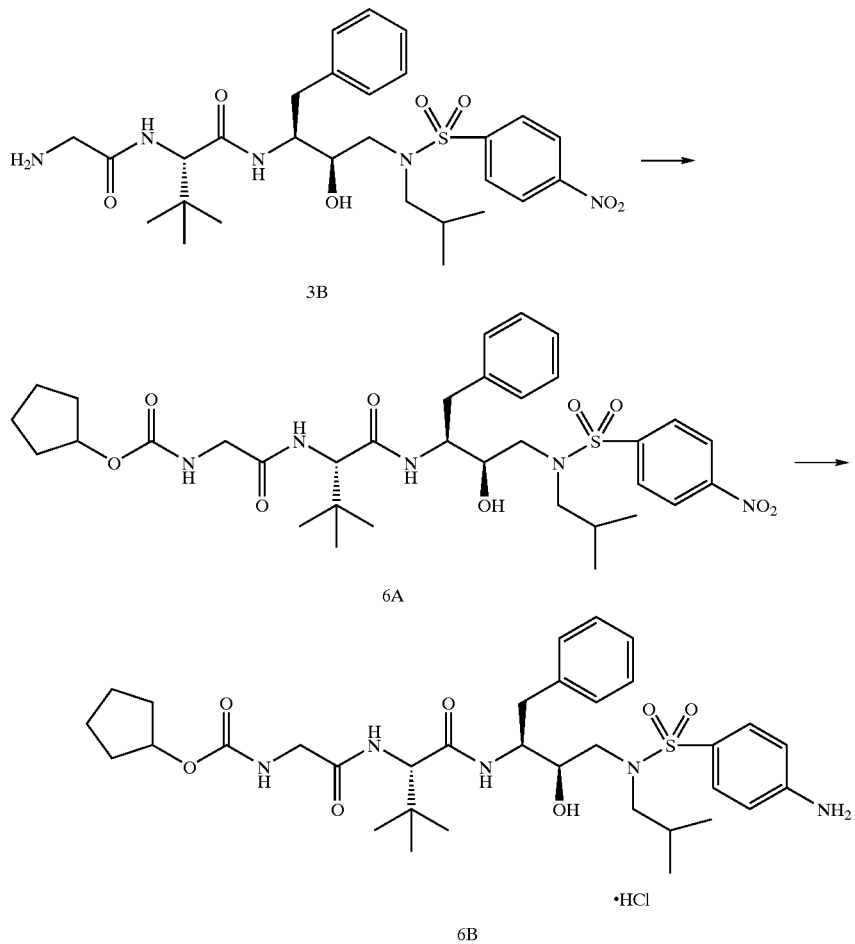
Scheme 6
Example 6A
Prepared from the amine 3B and cyclopentyl chloroformate following the procedure described for Example 4A: ESI m/z: 726 (M+Na$^+$, 100%);
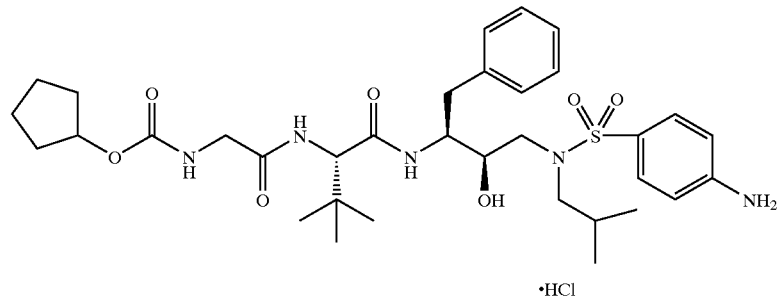

Example 6B
Prepared from the carbamate 6A following the procedure described for Example 3D: CIMS (NH$_3$) m/z: 674 (M+H$^+$).
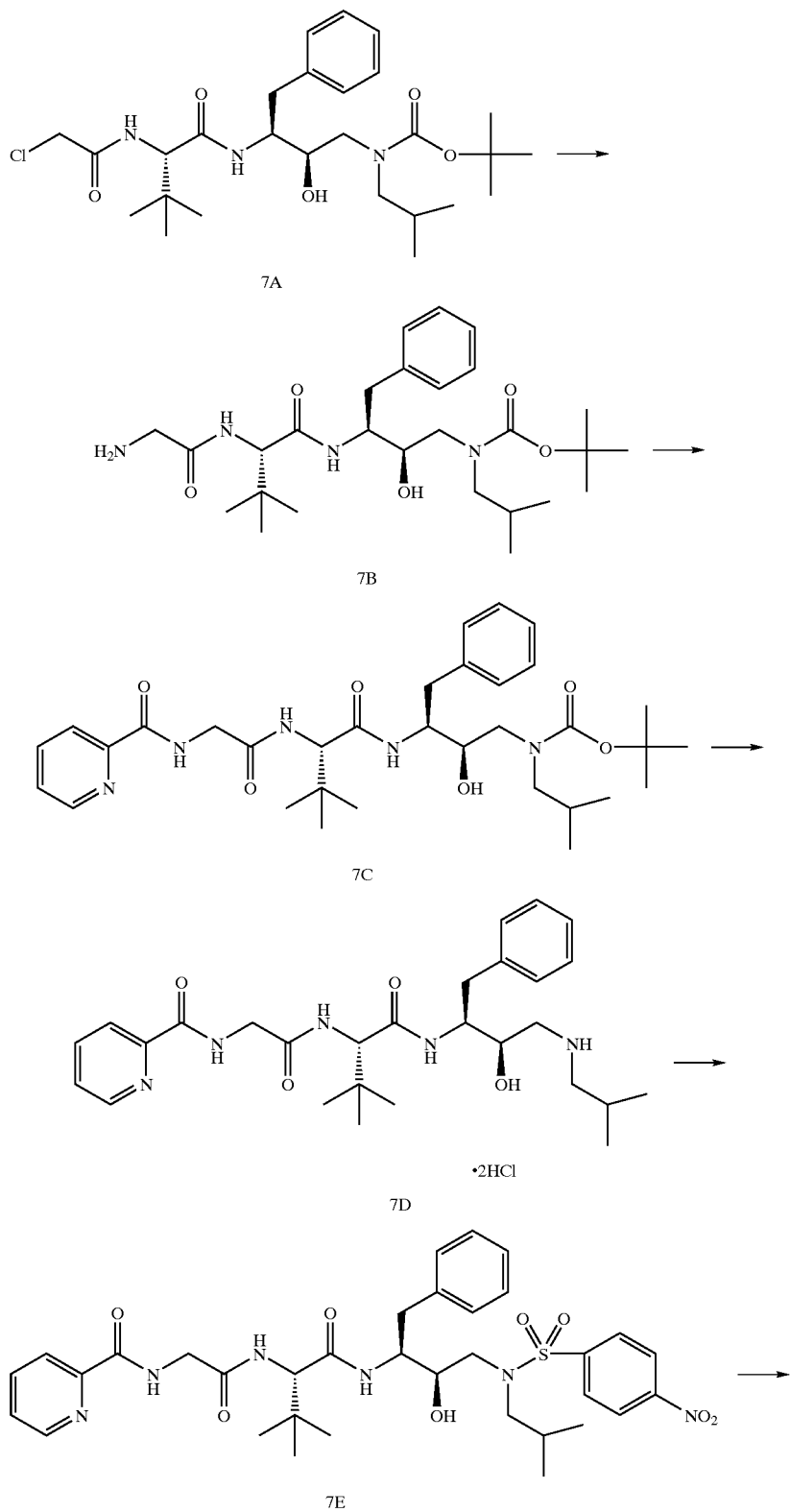
Scheme 7

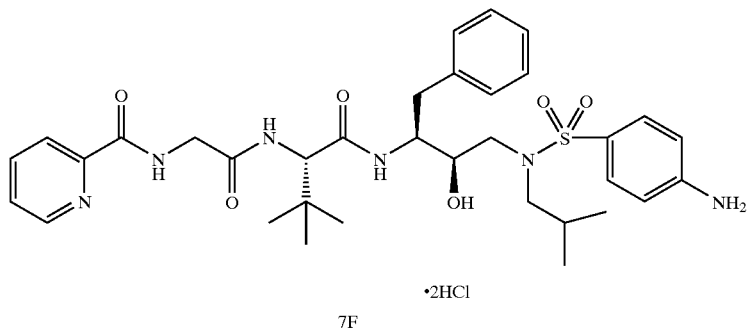

7F

Example 7B

Prepared from tert-butyl 3-{[N-(chloroacetyl)-3-methyl-L-valyl]amino}-2-hydroxy-4-phenylbutyl(isobutyl) carbamate 7A following the procedure described for Example 1B: APcI m/z: 507 (M+H$^+$, 100%)

Example 7C

To a solution of picolinic acid (60 mg, 0.49 mmol) in THF (2 mL) was added 1,1'-carbonyldiimidazole (80 mg, 0.49 mmol). The amine 7B (200 mg, 0.39 mmol) was added and the solution was stirred overnight. The mixture was diluted with EtOAc, was washed with water, and was dried (MgSO$_4$). The solvent was removed under reduced pressure to give the amide 7C as a white solid (239 mg, 99%): CIMS (NH$_3$) m/z: 612 (M+H$^+$).

Example 7D

A solution of carbamate 7C (239 mg, 0.39 mmol) and 4N HCl in dioxane (2 mL) was stirred 2 h. The solvent was removed under reduced pressure to give the amine salt 7D as a white solid (220 mg, 96%): CIMS (NH$_3$) m/z: 512 (M+H$^+$).

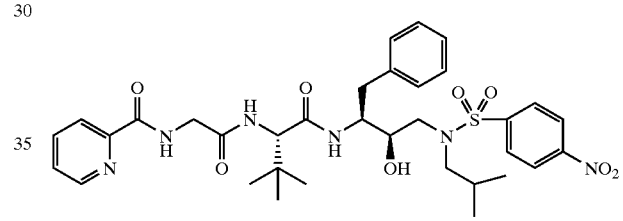

7E

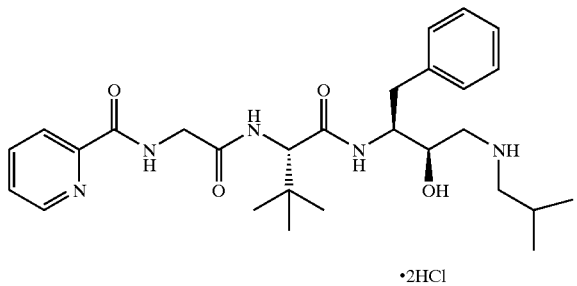

7D

Example 7E

To a solution of amine 7D (220 mg, 0.39 mmol) in THF (8 mL) and water (8 mL) was added 4-nitrobenzenesulfonyl chloride (97 mg, 0.44 mmol) and potassium carbonate (323 mg, 2.34 mmol). After stirring 3 h, ethyl acetate was added and the solution was washed with water, brine, and was dried (MgSO$_4$) . The solvent was removed under reduced pressure and the residue was chromatographed (silica gel, 5% methanol/CH$_2$Cl$_2$) to give the sulfonamide 7E as a white solid (112 mg, 41%): APcI m/z: 697 (M+H$^+$)

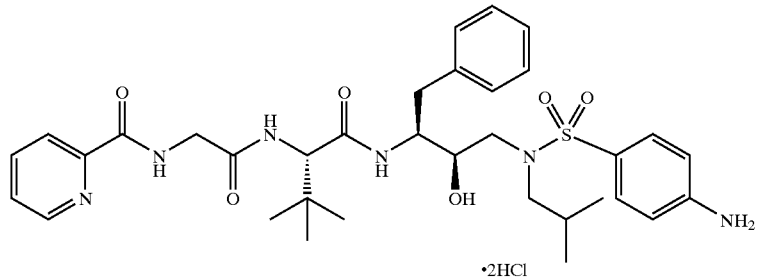

7F

Example 7F

Prepared from sulfonamide 7E following the procedure described for Example 3D: ESI m/z: 689 (M+Na+, 100%).

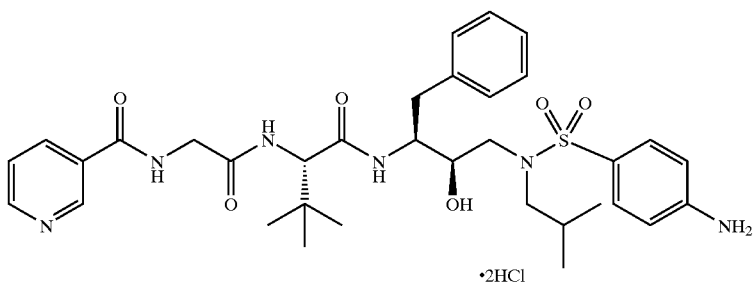

7G

·2HCl

Example 7G

Prepared from the amine 7B and nicotinic acid following the procedures described for Example 7C, 7D, 7E and 7F: ESI m/z: 689 (M+Na+, 100%);

Utility

The compounds of formula I, II and III possess HIV protease inhibitory activity and are therefore useful as antiviral agents for the treatment of HIV infection and associated diseases. The compounds of formula I, II and III possess HIV protease inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula I, II and III of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV protease, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV protease, the compounds of the present invention may also be useful as diagnostic reagents in diagnostic assays for the detection of HIV protease. Thus, inhibition of the protease activity in an assay (such as the assays described herein) by a compound of the present invention would be indicative of the presence of HIV protease and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

HIV RNA Assay
DNA Plasmids and in vitro RNA Transcripts

Plasmid pDAB 72 containing both gag and pol sequences of BH10 (bp 113-1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe was complementary to nucleotides 889–912 of HXB2 and the pol biotinylated capture probe was complementary to nucleotides 2374–2395 of HXB2. Alkaline phosphatase conjugated oligonucleotides used as reporter probes were prepared by Syngene (San Diego, Calif.). The pol reporter probe was complementary to nucleotides 2403–2425 of HXB2. The gag reporter probe was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 μM stocks in 2×SSC (0.3 M NaCl, 0.03 M sodium citrate), 0.05 M Tris pH 8.8, 1 mg/mL BSA. The biotinylated capture probes were prepared as 100 μM stocks in water. For details of the probes, see WO00/42060 which is hereby incorporated by reference.

Streptavidin Coated Plates

Streptavidin coated plates were obtained from Du Pont Biotechnology Systems (Boston, Mass.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM L-glutamine and 50 μg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1 (RF) stocks were 1–3×10⁷ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in Dulbecco's modified Eagles medium with 5% FCS for infection in microtiter plates. Virus was added and culture continued for 3 days at 37° C.

HIV RNA Assay

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Tritonx 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer δ (2.5 M diethanolamine pH 8.9 (JBL Scientific), 10 mM $MgCl_{2,}$ 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 µg/mL. $IC_{90}$ values of other antiviral compounds, both more and less potent than ddC, were reproducible using several stocks of HIV-1 (RF) when this procedure was followed. This concentration of virus corresponded to $\sim 3\times10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 µg/mL. Finally, the plateau level of viral RNA produced by an effective protease inhibitor should be less than 10% of the level achieved in an uninhibited infection. A compound was considered active if its $IC_{90}$ was found to be less than 1 µM.

For antiviral potency tests, all manipulations in microtiter plates, following the initial addition of 2× concentrated compound solution to a single row of wells, were performed using a Perkin Elmer/Cetus ProPette.

Dosage and Formulation

The antiviral compounds of this invention can be administered as treatment for viral infections by any means that produces contact of the active agent with the agent's site of action, i.e., the viral protease, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed:

1. A compound of formula I:

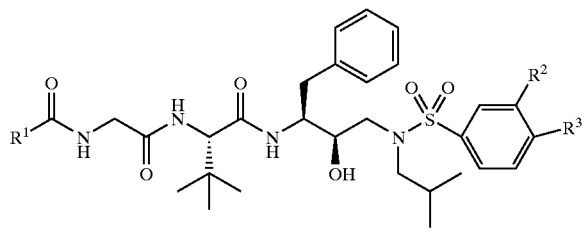

I or a pharmaceutically acceptable salt form thereof, wherein:

$R^1$ is selected from $R^4$ and —O—$R^4$;

$R^2$ and $R^3$ are selected from H and $NH_2$, or alternatively, $R^2$ and $R^3$ together form —$OCH_2O$— or —$CH_2CH_2O$—; and $R^4$ is selected from methyl, ethyl, propyl, isopropyl, butyl, i-butyl, t-butyl, phenyl, benzyl, cyclopentyl, 2-aminophenyl, 3-aminophenyl, 4-aminophenyl, 2-pyridyl, 3-pyridyl, and 4-pyridyl.

2. The compound of claim 1, wherein $R^2$ is H; and $R^3$ is $NH_2$.

3. The compound of claim 2, wherein $R^4$ is selected from i-propyl, phenyl, cyclopentyl, 2-pyridyl and 3-pyridyl.

4. The compound of claim 3, wherein $R^1$ is $R^4$; and $R^4$ is i-propyl.

5. The compound of claim 3, wherein $R^1$ is $R^4$; and $R^4$ is phenyl, cyclopentyl, 2-pyridyl and 3-pyridyl.

6. The compound of claim 3, wherein $R^1$ is —O—$R^4$; and $R^4$ is cyclopentyl.

7. The compound of claim 1, wherein the compound is of Formula II:

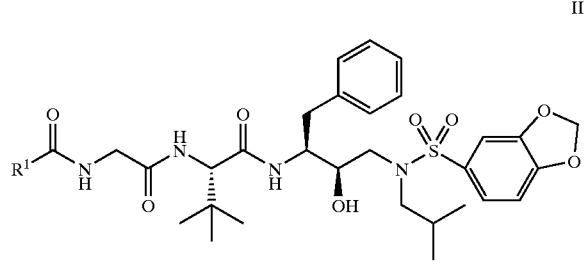

II or a pharmaceutically acceptable salt thereof.

8. The compound of claim 7, wherein $R^1$ is $R^4$; and $R^4$ is methyl, ethyl, i-propyl, t-butyl, phenyl, and i-butyl.

9. The compound of claim 7, wherein
   $R^1$ is —O—$R^4$; and
   $R^4$ is methyl, ethyl, i-propyl, cyclopentyl, phenyl, and benzyl.

10. The compound of claim 1, wherein the compound is of Formula III:

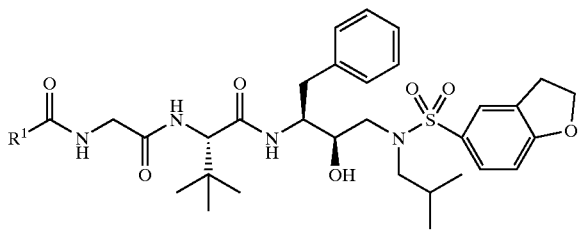

III or a pharmaceutically acceptable salt thereof.

11. The compound of claim 10, wherein
    $R^1$ is $R^4$; and
    $R^4$ is methyl, ethyl, and i-butyl.

12. The compound of claim 10, wherein
    $R^1$ is —O—$R^4$; and
    $R^4$ is ethyl and i-propyl.

13. The compound of claim 7, wherein
    $R^1$ is $R^4$; and
    $R^4$ is selected from 2-aminophenyl, 3-aminophenyl, 4-aminophenyl, 2-pyridyl, 3-pyridyl, and 4-pyridyl.

14. The compound of claim 1 or a pharmaceutically acceptable salt form thereof, wherein the compound is selected from:

N-[(1-{3-[(4-Amino-benzenesulfonyl)-isobutyl-amino]-1-benzyl-2-hydroxy-propylcarbamoyl}-2,2-dimethyl-propylcarbamoyl)-methyl]-nicotinamide;

Pyridine-2-carboxylic acid [(1-{3-[(4-amino-benzenesulfonyl)-isobutyl-amino]-1-benzyl-2-hydroxy-propylcarbamoyl}-2,2-dimethyl-propylcarbamoyl)-methyl]-amide;

[(1-{3-[(4-Amino-benzenesulfonyl)-isobutyl-amino]-1-benzyl-2-hydroxy-propylcarbamoyl}-2,2-dimethyl-propylcarbamoyl)-methyl]-carbamic acid cyclopentyl ester;

[(1-{1-Benzyl-3-[(2,3-dihydro-benzofuran-5-sulfonyl)-isobutyl-amino]-2-hydroxy-propylcarbamoyl}-2,2-dimethyl-propylcarbamoyl)-methyl]-carbamic acid isopropyl ester;

[(1-{1-Benzyl-3-[(2,3-dihydro-benzofuran-5-sulfonyl)-isobutyl-amino]-2-hydroxy-propylcarbamoyl}-2,2-dimethyl-propylcarbamoyl)-methyl]-carbamic acid ethyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid benzyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid phenyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid phenyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid cyclopentyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid isopropyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid ethyl ester;

[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-carbamic acid methyl ester;

N-[(1-{3-[(4-Amino-benzenesulfonyl)-isobutyl-amino]-1-benzyl-2-hydroxy-propylcarbamoyl}-2,2-dimethyl-propylcarbamoyl)-methyl]-benzamide;

N-{3[(4-Amino-benzenesulfonyl)-isobutyl-amino]-1-benzyl-2-hydroxy-propyl}-2-(2-isobutyrylamino-acetylamino)-3,3-dimethyl-butyramide;

N-{1-Benzyl-2-hydroxy-3-[isobutyl-(4-nitro-benzenesulfonyl)-amino]-propyl}-2-(2-isobutyrylamino-acetylamino)-3,3-dimethyl-butyramide;

N-{1-Benzyl-3-[(2,3-dihydro-benzofuran-5-sulfonyl)-isobutyl-amino]-2-hydroxy-propyl}-3,3-dimethyl-2-[2-(3-methyl-butyrylamino)-acetylamino]-butyramide;

N-{1-Benzyl-3-[(2,3-dihydro-benzofuran-5-sulfonyl)-isobutyl-amino]-2-hydroxy-propyl}-3,3-dimethyl-2-(2-propionylamino-acetylamino)-butyramide;

2-(2-Acetylamino-acetylamino)-N-{1-benzyl-3-[(2,3-dihydro-benzofuran-5-sulfonyl)-isobutyl-amino]-2-hydroxy-propyl}-3,3-dimethyl-butyramide;

N-[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-isonicotinamide;

N-[(1-(3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-nicotinamide;

Pyridine-2-carboxylic acid [(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-amide;

4-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

3-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

2-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

2-Amino-N-[(1-{3-[(benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

N-{3-[(Benzo[1,3]dioxole-5-sulfonyl)-isobutyl-amino]-1-benzyl-2-hydroxy-propyl}-3,3-dimethyl-2-[2-(3-methyl-butyrylamino)-acetylamino]-butyramide;

N-[(1-{3-[(Benzo[1,3]dioxole-5-sulfonyl)-isobutyl-amino]-1-benzyl-2-hydroxy-propylcarbamoyl}-2,2-dimethyl-propylcarbamoyl)-methyl]-benzamide;

N-{3-[(Benzo[1,3]dioxole-5-sulfonyl)-isobutyl-amino]-1-benzyl-2-hydroxy-propyl}-2-[2-(2,2-dimethyl-propionylamino)-acetylamino]-3,3-dimethyl-butyramide;

N-{3-[(Benzo[1,3]dioxole-5-sulfonyl)-isobutyl-amino]-1-benzyl-2-hydroxy-propyl}-3,3-dimethyl-2-(2-propionylamino-acetylamino)-butyramide;

2-(2-Acetylamino-acetylamino)-N-{3-[(benzo[1,3]dioxole-5-sulfonyl)-isobutyl-amino]-1-benzyl-2-hydroxy-propyl}-3,3-dimethyl-butyramide; and N-{3-[(Benzo[1,3]dioxole-5-sulfonyl)-isobutyl-amino]-1-benzyl-2-hydroxy-propyl}-2-(2-isobutyrylamino-acetylamino)-3,3-dimethyl-butyramide.

15. A pharmaceutical composition, comprising: a pharmaceutically acceptable carrier and a therapeutically effective amount of a compound according to claim 1.

16. A method for treating HIV infection, comprising: administering to a host in need of such treatment a therapeutically effective amount of a compound according to claim 1, or a pharmaceutically acceptable salt form thereof.

17. A method of treating HIV infection which comprises administering, in combination, to a host in need thereof a therapeutically effective amount of:
(a) a compound according to claim 1 or stereoisomeric forms, mixtures of stereoisomeric forms, or pharmaceutically acceptable salts thereof; and,
(b) at least one compound selected from the group consisting of HIV reverse transcriptase inhibitors and HIV protease inhibitors.

18. A method according to claim 17, wherein the reverse transcriptase inhibitor is selected from the group AZT, ddC, ddI, d4T, 3TC, delavirdine, efavirenz, nevirapine, trovirdine, MKC-442, HBY 097, ACT, UC-781, UC-782, RD4-2025, and MEN 10979 and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

19. A method according to claim 18, wherein the reverse transcriptase inhibitor is selected from the group AZT, efavirenz, and 3TC and the protease inhibitor is selected from the group saquinavir, ritonavir, nelfinavir, and indinavir.

20. A method according to claim 18, wherein compound (b) is ritonavir.

* * * * *